(12) United States Patent
Mishkin et al.

(10) Patent No.: US 10,744,251 B2
(45) Date of Patent: Aug. 18, 2020

(54) DOUBLE FIBER BUNDLE DIALYZER

(71) Applicant: MIRIMEDICAL LLC, Gaithersburg, MD (US)

(72) Inventors: Gary Mishkin, Gaithersburg, MD (US); Mark Scott Goodin, Solon, OH (US)

(73) Assignee: MIRIMEDICAL LLC, Potomac, MD (US)

( * ) Notice: Subject to any disclaimer, the term of this patent is extended or adjusted under 35 U.S.C. 154(b) by 64 days.

(21) Appl. No.: 15/550,866

(22) PCT Filed: Feb. 12, 2015

(86) PCT No.: PCT/US2015/015599
§ 371 (c)(1),
(2) Date: Aug. 14, 2017

(87) PCT Pub. No.: WO2016/130128
PCT Pub. Date: Aug. 18, 2016

(65) Prior Publication Data
US 2018/0028739 A1    Feb. 1, 2018

(51) Int. Cl.
*A61M 1/16*    (2006.01)
*A61M 1/34*    (2006.01)
*B01D 63/04*    (2006.01)

(52) U.S. Cl.
CPC ............ *A61M 1/1633* (2014.02); *A61M 1/16* (2013.01); *A61M 1/3417* (2014.02); *B01D 63/043* (2013.01); *A61M 2230/207* (2013.01); *B01D 2313/20* (2013.01); *B01D 2313/21* (2013.01); *B01D 2319/022* (2013.01); *B01D 2319/06* (2013.01)

(58) Field of Classification Search
CPC ...... B01D 61/24; B01D 61/243; B01D 61/28; B01D 61/30; B01D 61/32; B01D 63/02; B01D 63/04; B01D 63/043; B01D 2313/21; B01D 2313/44; B01D 2313/20; B01D 2313/13; B01D 2313/08; B01D 2313/10; B01D 2313/12; B01D 2319/02; B01D 2319/022; B01D 2319/06; A61M 1/16; A61M 1/3417; A61M 1/3434; A61M 1/342; A61M 1/1633; A61M 1/34; A61M 1/3413; A61M 1/1601; A61M 1/3465; A61M 2230/207
See application file for complete search history.

(56) References Cited

U.S. PATENT DOCUMENTS

| | | |
|---|---|---|
| 4,227,295 A | 10/1980 | Bodnar et al. |
| 5,700,372 A | 12/1997 | Takesawa et al. |
| 6,315,895 B1 | 11/2001 | Summerton et al. |
| 6,406,631 B1 | 6/2002 | Collins et al. |

(Continued)

*Primary Examiner* — Pranav N Patel
(74) *Attorney, Agent, or Firm* — Browdy and Neimark, P.L.L.C.

(57) ABSTRACT

A dialyzer composed of: first and second dialyzation chambers, and an intermediate chamber interposed between the first and second dialyzation chambers. Each of the chambers has a respective one of a blood inlet or outlet and a dialysate inlet or outlet arranged so that blood and dialysate flow in counter-current to one another in both chambers. The intermediate chamber is connected to form a dialysate-free blood flow passage between the blood chambers and is configured to maintain a substantially uniform blood flow.

4 Claims, 7 Drawing Sheets

(56) References Cited

U.S. PATENT DOCUMENTS

| | | |
|---|---|---|
| 8,883,008 B2 | 11/2014 | Mishkin |
| 2004/0127842 A1* | 7/2004 | Collins ................ B01D 61/142 604/6.09 |
| 2011/0120930 A1* | 5/2011 | Mishkin .................. A61M 1/16 210/252 |

* cited by examiner

DOUBLE FIBER BUNDLE DIALYZER

STATEMENT REGARDING FEDERALLY SPONSORED RESEARCH OR DEVELOPMENT

This invention was made with government support under 5R42DK64500 awarded by National Institutes of Health (NIH), Bethesda, Md. The government has certain rights in the invention.

CROSS-REFERENCE TO RELATED APPLICATION

This application relates to improvements in inventions disclosed in copending U.S. application Ser. No. 13/054,306, filed on Jan. 14, 2011, the disclosure of which is incorporated herein by reference.

BACKGROUND OF THE INVENTION

The present invention relates to improvements in dialyzers, and particularly single-unit dialyzers that can be used with all existing dialysis equipment to provide dialytic therapies having increased efficiency.

This invention particularly relates to improvements in dialyzers of the type disclosed in U.S. Patent Pub. 2011-0120930 A1, the disclosure of which is incorporated herein by reference and portions of which are reproduced herein.

The dialyzer disclosed therein is composed of two bundles of hollow fibers constituted by semi-permeable membranes, preferably housed within a single casing that delimits, in effect, two chambers. The dialyzer further includes an intermediate chamber in which blood flows from one fiber bundle to the other so that the blood coming from the first fiber bundle becomes intermixed and thus homogenized. This dialyzer is arranged to be connected to a standard dialysis machine via a blood inlet and outlet and a dialysate inlet and outlet. Dialysate flows between the chambers via a flow restricting passage that produces a dialysate pressure drop between the chambers delimited in the casing.

BRIEF SUMMARY OF THE INVENTION

The invention relates particularly to improving the dialyzer performance by providing a constricted passage between the two chambers that is dimensioned to provide a dialysate pressure drop that improves dialyzer performance, particularly at low dialysate flow rates, and by the provision of a novel end cap defining the intermediate chamber.

DETAILED DESCRIPTION OF THE INVENTION

Figure 1:
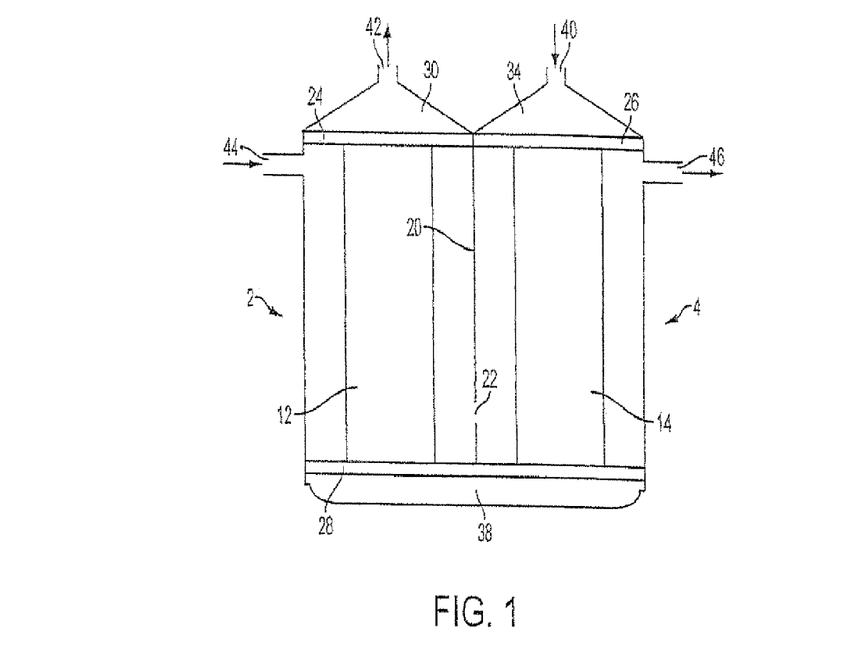
FIG. 1 is a simplified, elevational, pictorial view of one embodiment of the dialyzer disclosed in U.S. Patent Pub. 2011-0120930 A1.

FIG. 1 shows one embodiment of the dialyzer disclosed in U.S. Patent Pub. 2011-0120930 A1. This apparatus is composed, in effect, of an outer casing that delimits two dialyzation chambers 2, 4 that may be disposed, effectively, side by side. Each dialyzation chamber 2, 4 is closed off by a respective part of the outer casing and manifolds 24, 26, 28, to be described below. Each dialyzation chamber contains a filter member in the form of a bundle 12, 14, respectively, of semi-permeable hollow membrane fibers. Each fiber has the form of a small diameter hollow tube. The outer casing parts have a common wall 20, the common wall being provided, near the bottom of the outer casing, with an opening, or passage, 22 forming a constricted passage for dialysate flow.

Manifold 24 is provided with openings that place the upper ends of the fibers of bundle 12 in communication with a blood outlet compartment 30, while manifold 26 is provided with openings that place the upper ends of the fibers of bundle 14 in communication with a blood inlet compartment 34. Compartments 30 and 34 are delimited by header caps.

Manifold 28 is provided with openings that place the lower ends of the fibers of bundles 12 and 14 in communication with an intermediate chamber 38 in which blood flows from the fibers of bundle 14 to the fibers of bundle 12 while blood from the various fibers become intermixed so that the blood entering the fibers of bundle 12 is of a more uniform composition. The component delimiting chamber 38 may be a further header cap.

Manifolds 24, 26 and 28 close off the portions of each chamber 2, 4 through which dialysate flows so that dialysate cannot flow into chamber 38.

Figure 2:
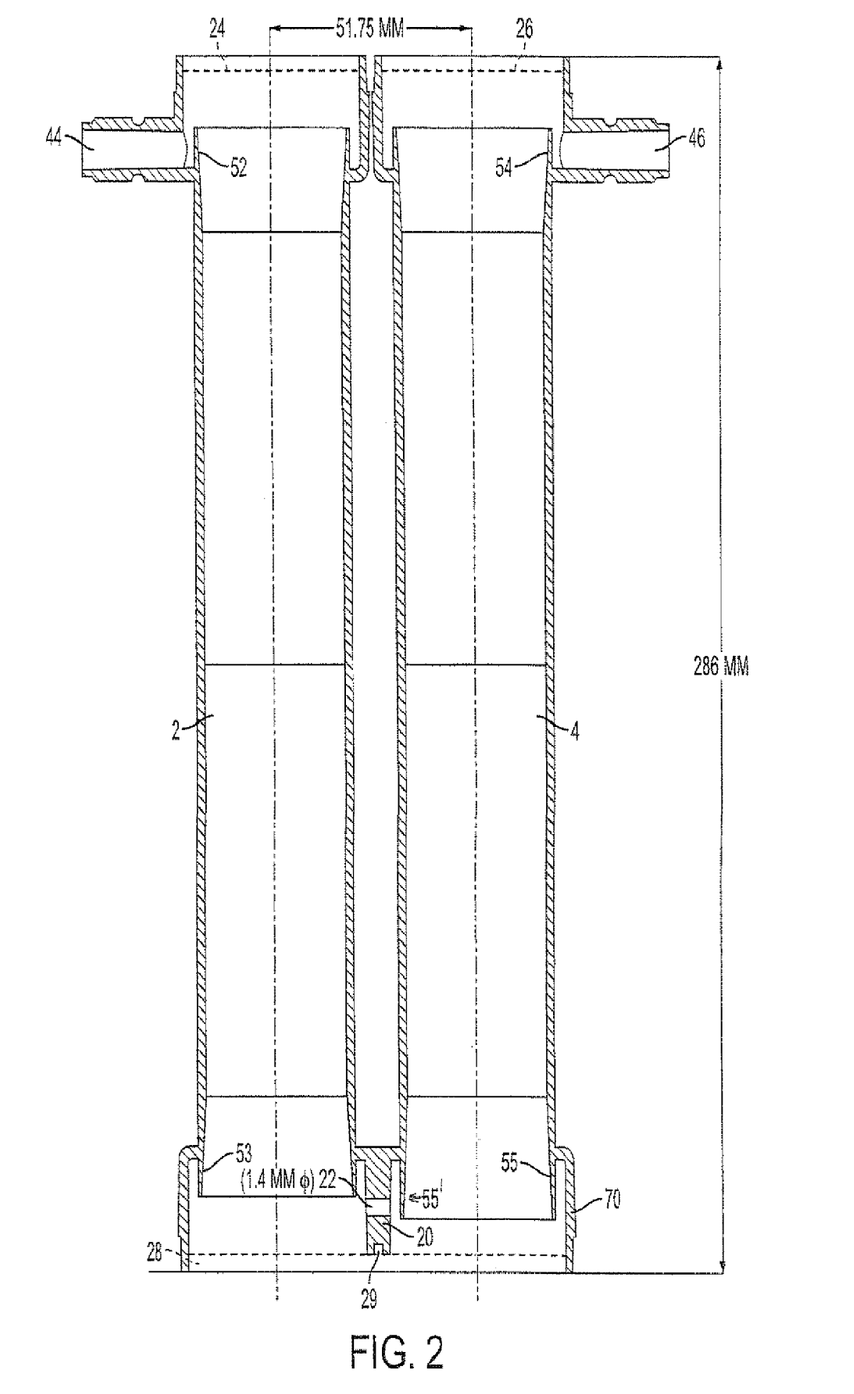
FIG. 2 is an elevational, cross-sectional view of the casing according having an improved constricted passage or flow restrictor, according to a preferred embodiment of the present invention.

FIG. 2 is a cross-sectional view of one preferred embodiment of the outer casing of a dialyzer according to the present invention. This embodiment is composed essentially of two circularly cylindrical tubes delimiting the dialyzation chambers 2, 4. Common wall 20 with opening 22 is provided at the lower end of the outer casing. The lower end of common wall 20 is provided with a recess 29 constructed to mate with a mating projection of the end cap that delimits intermediate chamber 38. Opening 22 is a constricted passage producing a pressure drop in the dialysate flow. The function of the constricted passage is to increase the dialysate side pressure to force backfiltration in chamber 2, while yielding a lower dialysate side pressure to force ultrafiltration in chamber 4. By way of example, opening 22 may have a circular cross section with a maximum diameter of the order of 2.5 mm, or a diameter of 0.5 to 2.5 mm, or 2.0-2.5 mm, or 0.5 to 0.99 mm, more preferably 0.5 to 0.9 mm, and still more preferably 0.6 to 0.9 mm or 0.6 to 0.8 mm, the latter range having been found to maximize the dialyzer performance at dialysate flow rates of 200-400 ml/mm by maintaining a higher dialysate pressure in chamber 2 and a lower dialysate pressure in chamber 4.

At dialysate flows of 600 ml/min and higher, a diameter of 0 mm for opening 22 will provide a pressure drop that will produce a useful result. At flows below 600 ml/min, a 2.0 mm opening is too large and there is not enough of a pressure drop to cause the desired filtration/backfiltration.

The effect produced by opening 22 also depends on its length, i.e., in the direction of its longitudinal axis. A length of at least 2.0 mm is sufficient and allows to "fine tune" the pressure drop with an opening having a constant radius. Lengths greater than 20 mm will require the fiber bundles in the two chambers to be too far apart. It presently appears that a length between 4-10 mm will produce the best results.

Opening 22 may have, for example, a longitudinal axis that has a length of the order of 5.7 mm, and is inclined at an angle of the order of 60°-90° to the longitudinal axis of each chamber 2, 4, an angle of 90° presently being preferred, as shown, and being oriented to produce a flow having a direction with a component perpendicular to the direction of dialysate flow in chamber 4. Flow through the opening is dictated by the Hagen-Poiseuille equation, inversely proportional to the length of the opening and related by $r^4$ to the radius (r) of the opening. The length of the opening, therefore, will facilitate the control of the pressure drop across the chambers, and will provide tighter control compared to small changes in the radius.

Also by way of example, the overall length of the outer casing may be of the order of 28.6 cm and the distance between the longitudinal axes of chambers 2 and 4 may be of the order of 5.2 cm.

The diameter of each chamber 2, 4 is of the order of 3.6 cm at the center of the chamber. However, other diameter values can be used. In general, the diameter of the chamber will be related to the size of the fiber bundle. As a rule of thumb, the total area of the fibers in a bundle, based on the outer diameters of all of the fiber OD in one plane, should preferably be approximately 50-55% of the cross-sectional area of the chamber in the same plane.

The locations of manifolds 24, 26 and 28 are shown in broken lines in FIG. 2.

Figure 3:
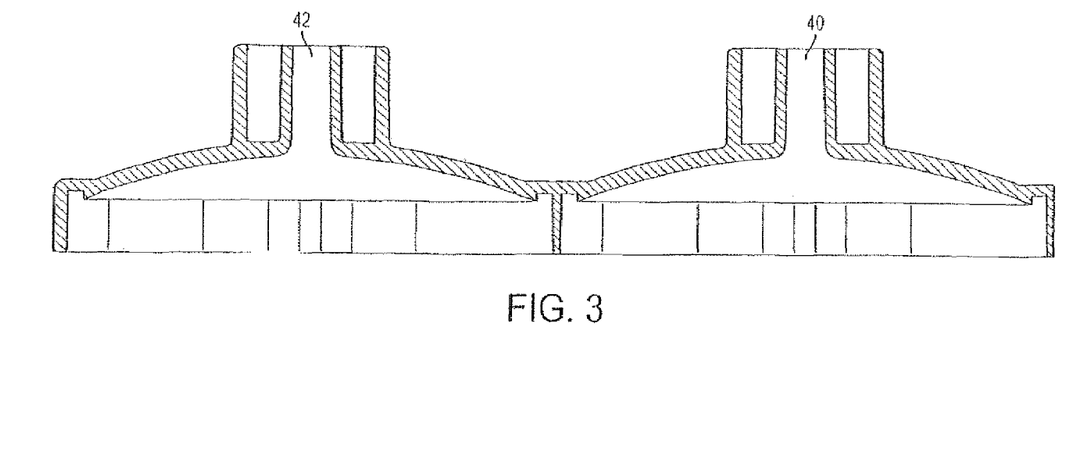
FIG. 3 is an elevational, cross-sectional view of top header caps of the dialyzer disclosed in U.S. Patent Pub. 2011-0120930 A1.

FIG. 3 shows an example of top header caps delimiting compartments 30 and 34.

Referring back to FIGS. 1 and 2, the volumes enclosed by the fibers of bundles 12 and 14 define respective blood compartments in chambers 2 and 4, while the volumes surrounding the fibers of bundles 12 and 14 define respective dialysate compartments in chambers 2 and 4.

Manifolds 24, 26 and 28 constitute walls that close off the upper ends of the dialysate compartments and manifold 28 constitutes a wall that close off the lower ends of the dialysate compartments. The lower end of common wall 20 bounds constricted passage 22 between the two dialysate compartments.

Compartment 34 is provided with an inlet passage 40 for the delivery of blood into the apparatus, while compartment 30 has a blood outlet 42 for removal of blood from the apparatus. In addition, chamber 2 is provided with a dialysate inlet 44, while chamber 4 is provided with a dialysate outlet 46.

During a dialysis procedure, fresh dialysate is introduced through inlet 44 into the dialysate compartment in chamber 2, flows through opening, or restricted passage, 22 near the bottom of common wall 20 into the dialysate compartment in chamber 4, and then out through outlet 46. At the same time, blood that is to be dialyzed is introduced into chamber 34 via inlet 40, flows through the fibers of bundle 14 into intermediate chamber 38, and then flows through the fibers of bundle 12 to chamber 30 and finally exits the apparatus through outlet 42.

In chamber 4, plasma water is removed from blood flowing through the fibers of bundle 14 and is transferred into the dialysate compartment in chamber 4 by being filtered across the semipermeable membranes forming the walls of the fibers of bundle 14.

Upon exiting the blood compartment in chamber 4, the blood enters and flows through intermediate chamber 38 and then into the blood compartment in chamber 2.

As the blood flows through the blood compartment in chamber 2, i.e., through the fibers of bundle 12, fresh dialysate is filtered from the dialysate compartment, across the semipermeable membranes forming the walls of the fibers of bundle 12 and into the blood compartment of chamber 2 at a rate substantially equal to the rate at which plasma water was filtered from the blood compartment of chamber 4. The manner in which the filtration rates are controlled will be described below.

Thus, ultrafiltration is performed in chamber 4, while substitution fluid is introduced from fresh dialysate into the blood compartment in chamber 2 via backfiltration. The dialyzer is thus capable of achieving a high rate of ultrafiltration with the introduction of substitution fluid by backfiltration that results in an on-line Hemodiafiltration (HDF) treatment. HDF is a hemodialysis modality that combines the use of dialysis fluid for the diffusive removal of toxins with larger volumes of ultrafiltration (compared to standard hemodialysis) to remove middle weight molecules by convection.

Fresh dialysate fluid for this system may be generated using existing methods and standard dialysis equipment. The dialysate fluid enters the dialysate compartment in chamber 2 and flows in counter-current with respect to the blood flow. This dialysate fluid performs two functions: 1) it acts to set up a concentration gradient relative to the blood compartment, thereby inducing diffusion of solutes across the semi-permeable membranes from the blood compartment to the dialysate compartment in chamber 2; and 2) because of the relatively higher pressure of the incoming dialysate compared to the blood compartment pressure, it produces a backfiltration of dialysate into the blood compartment.

Upon exiting chamber 2, the dialysate fluid enters the dialysate compartment in chamber 4, still flowing in counter-current with respect to the blood flow in the respective blood compartment. The dialysate flow rate increases as the dialysate flows through the dialysate compartment in chamber 4, due to filtration of plasma water from the blood compartment across the semi-permeable membranes of the fibers of bundle 14.

Dialysate also flows around the fibers of each fiber bundle, entering at one side of the respective dialysate chamber and flowing diagonally across the chamber and around the membrane fibers before exiting at the other side, and the other end, of the respective chamber. This flow across, or around, both fiber bundles may enhance fiber surface contact and diffusive removal of substances.

Upon exiting the dialyzer, the spent or used dialysate is transported back to the dialysis machine and to the drain in a conventional manner.

The fibers of both bundles may be of the same material and both bundles also have the purpose of diffusive removal of toxins. It is also possible, at high protein concentrations in the blood, that some backfiltration starts in fiber bundle 14.

The volumetric control of a dialysis machine ensures proper ultrafiltration and controls the rates of filtration and backfiltration. The fiber bundle involved in the backfiltration, in chamber 2, acts as a final fluid quality filter and has been shown to bring both bacteria and endotoxin to levels that approach pharmaceutical grade fluids.

One advantage of this system is that small molecules such as urea can be removed efficiently due to the appropriately large surface area of the two fiber bundles, and midsized molecules are removed efficiently due to the large filtration with backfiltration, which is optimized with this double fiber bundle configuration. No additional dialyzers, no final ultrafilters, no additional pumps or external equipment and no external substitution fluid are required.

The rate of filtration and backfiltration will be controlled by the resultant pressures due to the blood and dialysate flow rates. This is discussed in U.S. Pat. No. 6,406,631, issued Jun. 18, 2002, the disclosure of which is incorporated herein by reference.

There are several advantages to the disclosed double fiber bundle dialyzer as compared with the prior art. First, the dialyzer according to the invention can be given a large membrane surface area that will result in improved urea and creatinine removal.

The largest dialyzer commercially available today has a membrane surface area of 2.5 $m^2$. Dialyzers employing known ultrafiltration technology would exhibit a tendency to clot if given a larger membrane surface area. In addition, if the filtration rate is too high in known dialyzers, an alarm indicating a reverse ultrafiltration error will be produced because the TMP (transmembrane pressure=average blood side pressure−average dialysate side pressure) becomes negative and implies fluid is fluxed across the membrane from the dialysate into the blood. In the past, when fluid quality was more questionable, this may have been a problem. Various dialysis machines measure TMP in different ways. Very few dialysis machines measure the blood in and blood out as well as the dialysate in and dialysate out pressures to get a true TMP. Most dialysis machines use the blood out and dialysate out pressures and an offset to calculate the TMP.

However, the novel technology on which the dialyzer disclosed herein is based makes possible a dialyzer having a membrane surface area of 3.0 $m^2$ or more. The double dialyzer configuration according to the present invention resolves the clotting issue as discussed herein, and also resolves the reverse ultrafiltration alarm problem by decreasing the dialysate out pressure due to the restricted passage between the dialysate compartments.

A similar configuration with a smaller fiber bundle size, for example a membrane surface area of 0.3-0.9 $m^2$ for each bundle, may also be used when the blood flow rate or dialysate flow rate is lower. The unit will need to be adjusted to accommodate this smaller size. This may be achieved by shortening the length of the unit and fiber bundles, or by reducing the number of fiber in each bundle or both. When reducing the number of fibers in each bundle, the width of each dialyzation chamber will need to be adjusted to maintain a packing density in each of the chambers between 50%-60%.

In addition, the rate of ultrafiltration and midsize molecule removal will be greater in the dialyzer according to the invention than in prior art systems having the same dialyzer area and similar Kuf, Kuf being the coefficient of ultrafiltration for the filter member, i.e., the rate of plasma water fluid flux across the membrane, or fiber wall, per hour per mmHg of transmembrane pressure (TMP). This is because the TMP is enhanced in the invention dialyzer by the two dialyzation chamber design.

Further, the dialysate distribution and resultant clearance will be better in dialyzers according to the invention, at least when crimped fibers are used for the membranes. Specifically, crimped fibers result in a more uniform dialysate flow throughout the dialyzer. This results in improved clearance of small molecules. Also, the provision of two separate dialysate compartments communicating via the restricted passage, or orifice, will help to redistribute the dialysate flows so any channeling, even with straight fibers, will be all but eliminated in the second dialysate compartment. Finally, spacer yarns have been incorporated in fiber bundles to also assist in proper dialysate distribution by encircling the fibers and preventing fibers from clumping together which will reduce effective surface area. A discussion of spacer yarns can be found at http://www.ncbi.nlm.nih.gov/pubmed/12918588.

If, in prior art systems, substitution fluid is not added, this dialyzer clots very quickly. The second stage will have a lower small molecule removal rate since the concentration gradient is smaller.

Furthermore, in prior art systems substitution fluid requires a separate filter for the fluid generated on-line and a separate pump to control infusion, making the system more complicated and expensive to run than a dialyzer according to the invention.

Specifically, dialyzers according to the invention are intended to be connected to standard dialysis machines that are already in dialysis clinics to perform an HDF treatment. To perform any of the other HDF treatments, prior art machines require a specialized structure that has extra sensors to measure the amount of filtration, separate pumps to return the substitution fluid and extra filters since they reinfuse the substitution fluid either directly into the blood line or into the header of the dialyzer. For example, these other systems will need to calculate the volume going into the system (blood and dialysate) and the volume coming out (blood and dialysate). The system needs to calculate the rates of filtration and then must add the proper amount of substitution fluid to the system to balance the fluid removed. So the equipment is complicated by balances or fluid control units that measure the fluid exchanged. This also requires a pump to infuse the substitution fluid directly into the blood line. Our system uses the existing fluid balancing system in the current machines. The fluid balancing system can be a diaphragm pump such as in the Frensius machines or flow meter controlled system such as in the Gambro machines.

An advantage of the present invention is that the double fiber bundle dialyzer can be used with any known dialysis machine with volumetric control to perform an HDF treatment without needing to set up additional infusion lines, filters and/or pumps or units.

Improved midsize molecule clearance is achieved in a dialyzer according to the invention by increasing filtration and backfiltration. More specifically, midsize molecules are removed more effectively by filtration (convection removal) and dialyzers according to the invention enhance convective removal by the action of the restricted dialysate passage 22 and by using the proper membranes.

Furthermore, a dialyzer according to the invention can be used in existing dialysis machines without the need for additional hardware or modifications.

For example, a dialyzer according to the invention can be used with known dialysis machines, such as a standard Fresenius machine, on which a dialyzer according to the invention was tested, in place of a conventional dialyzer, using the exact same set-up as for a standard dialysis treatment, including standard blood lines. The dialyzer according to the invention will automatically enhance the filtration and back filtration based on its design. Nearly all current dialysis machines have a place for an ultrafilter. This is a filter that filters the dialysate fluid prior to reaching the dialyzer. It is a component of a dialysis machine, possibly not needed in systems according to the present invention. An ultrafilter is usually a hollow fiber filter similar to a standard dialyzer, but is designed to have the fluid diffuse across the fibers (filtration) and then flow to the dialyzer. All machines marketed within the past 5 years or more have a built in ultrafilter (also called an endotoxin filter).

One important feature of the dialyzer according to the invention is that blood passes through and exits the fibers of bundle 14, then enters a large space, i.e., intermediate chamber 38, where the blood exiting all of the fibers of bundle 14 is mixed together before entering the fibers of bundle 12. No filtration, or back filtration, or substitution of fluid occurs in intermediate chamber 38; only blood flows through intermediate chamber 38.

Chamber 38 performs an important function that serves to eliminate, or at least minimize, the adverse effects of a common problem in dialysis known as "channeling". Channeling can occur on the dialysate side or the blood side of the fibers. Channeling on the blood side is when blood flows through different fibers at different rates. In the fibers in which a relatively fast flow occurs, the fibers see more blood than do the fibers in which a slower blood flow occurs, although ultrafiltration occurs from all of the fibers. In the fibers experiencing slow blood flow, while plasma water is being removed by ultrafiltration (raising the hematocrit: the proportion of blood volume that is occupied by red blood cells), the blood will tend to clot and the fibers will become blocked. This results in more flow through the other fibers and a reduction in the active filter surface area, i.e., the filter surface area participating in the filtering of toxins. A reduction in the active filter surface area of the dialyzer will reduce the efficiency of the dialyzer and the treatment. At the same time, the reduction in the active filter surface area causes a higher pressure at blood inlet 40, which in turn causes more ultrafiltration in the remaining fibers. This higher ultrafiltration will lead to more clotting.

Since systems according to the invention have two smaller bundles of fibers separated by intermediate chamber 38, as the blood goes through the fibers of bundle 14 it becomes more concentrated (because of ultrafiltration that filters plasma from the blood). However, all of the blood exiting the fibers of bundle 14 enters the common intermediate chamber 38 and mixes together. This will include the blood that flowed slowly through one or more fibers and the blood that flowed faster through other fibers. The blood entering the fibers of bundle 12 will, therefore, be more homogenous. The pressure of the blood entering the fibers of bundle 12 will also be the same at all of the fiber walls, leading to a more consistent backfiltration and reconstitution of the blood returning to the body at nearly the same hematocrit at which it was pumped out of the body.

To summarize, intermediate chamber space 38 in the double fiber bundle system according to the invention acts to mix the blood while no filtration, or back filtration, or substitution of fluid is occurring so that the blood entering the fibers of bundle 12 is homogenous and at nearly the same pressure from one fiber to another.

An exemplary preferred embodiment of the invention may have the following specific parameters:

Dimensions of each fiber: ID=180-200 μm; wall thickness=filter member 35-50 μm; OD=250-300 μm; length=28 cm±3 cm;

Effective surface area of each fiber bundle=1.5 m$^2$;

Number of fibers in each chamber, i.e., in each bundle=approximately 9500 fibers+/−500 fibers, the exact number depending on the diameter and length of the fibers.

The pore size for toxin removal should be selected to produce as sharp a drop as possible in the elimination rate of molecules at 65,000 or 66,000 Daltons (the universal mass unit or atomic mass unit). In many cases, little or no molecular weight substances above 65,000 or 66,000 Daltons should be removed. This will minimize protein losses during treatment. However, it may be desirable to provide a larger pore size to effect removal of some proteins and protein bound solutes.

One nonlimiting example of the membrane material of the fibers in bundles 12 and 14 would be a product marketed by Asahi Kasei Kuraray Medical Co., Ltd. under the trade names REXBRANE and Polysulfone APS, a polysulfone membrane with a hydrophilic gel layer.

The fibers should be crimped to enhance dialysate flow. This crimping gives the fibers a form that follows a sinuous path along their length, which is the form of the REXBRANE fibers.

Each fiber bundle may have a Kuf (Coefficient of Ultrafiltration) of 20-26 ml/h/(mmHg TMP), TMP can be calculated as the average pressure on the blood side of the membrane minus the average pressure on the dialysate side of the membrane. TMP is mostly determined by the hydrostatic pressure of the blood flow on the blood side of the membrane (favoring flux from the blood side to the dialysate side), the opposite pressure of the dialysate fluid on the dialysate side of the membrane (favoring dialysate fluid flux to the blood side) as well as the opposite pressure associated with the oncotic pressures (which is a form of osmotic pressure exerted by proteins in blood plasma that normally tends to pull water into the circulatory system) of the blood proteins (favoring fluid flux from the dialysate side to the blood side). As more fluid flows across a membrane from the blood side to the dialysate side, the oncotic pressures increase as the protein concentration increases due to less plasma water and a relatively higher protein concentration.

The true calculation of Kuf, therefore, can vary as a function of the protein concentrations, dialysate flows, and blood flows. The Kuf range given above was consistent for the specific embodiment tested using the Fresenius 2008 series dialysis machine and the blood and dialysate flows tested blood flow=300-550 ml/min and dialysate flow=800 ml/min). When the dialysate flow (Qd) is reduced to 500 ml/min, there is a drop in TMP (machine measured) of close to 100 mmHg in a dialyzer having an opening 22 with a diameter greater than 1.0 mm. This is due to the increase in average dialysate side pressures. The incoming dialysate pressures are nearly the same at 800 and 500 ml/min dialysate flows, the pressures being approximately 200 mmHg±dependent on blood flow.

The pressure drop between the inlet and outlet of the dialysate compartment in chamber 2 is slight due to the presence of the constricted passage between the dialysate compartments. The pressure drop across the constricted passage is lower with a 500 ml/min flow rate since the flow is lower. This yields a higher average pressure in the dialysate compartment of chamber 4 for a 500 ml/min dialysate flow than for an 800 ml/min flow. The higher pressure on the dialysate side of chamber 4 yields a drop in TMP.

Also, the conventional volumetric controller (not shown) of the dialysis machine to which the dialyzer is connected, which makes sure that the dialysate volume entering via inlet 44 is the same as the volume that leaves via outlet 46, can apply a slight negative pressure at outlet 46, thereby pulling fluid from the blood side to make the incoming and outgoing volumes the same. Additional fluid removal is normally programmed into the dialysis machine in order to remove the excess fluid a patient consumes between treatments. This excess fluid removal is controlled by a separate pump in all dialysis machines and works in conjunction with the present invention.

The Kuf (coefficient of ultrafiltration) is calculated for the fibers of bundle 14 only using human blood reconstituted with saline and bovine albumin at a concentration of ~6 g/dL (this also effects the measured Kuf. If it was measured with saline, the Kuf would be calculated to be much higher due to the lower viscosity and lack of blood proteins, i.e. albumin).

In chamber 2, the dialysate compartment pressure drop with Qd=800 ml/min (dialyzer with incoming dialysate from the associated machine and provided with the restricted passage beneath common wall 20 as well as back filtration) =about 15 mmHg (this is a slight pressure drop due to the constricted passage at the outlet of the dialysate compartment in chamber 2).

In chamber 4, the pressure drop across the dialysate compartment with Qd=800 ml/min (with a large filtration volume from blood to dialysate side, the machine volume controller can cause a negative pressure at the outlet 46=about 55 mmHg, with or without negative pressure at outlet 46, downstream of the restricted passage to outlet 46 (dialysate flows in counter-current to blood flow).

The pressure drop produced in passage 22 in common wall 20 between the dialysate compartments in chambers 2 and 4 causes a relatively high dialysate pressure to reign in chamber 2 and should preferably provide a pressure drop of approximately 100 mmHg at a Qd=400 ml/min, or a 50 mmHg drop with a Qd=200. The total dialysate pressure drop between the inlet 44 and outlet 46 should be about 150 mmHg. The rate of ultrafiltration and backfiltration can, therefore be controlled by the user by changing the dialysate flow rate. A higher flow rate increases the ultrafiltration and backfiltration, while lowering the dialysate flow reduces the ultrafiltration and backfiltration.

There is some variability dependent on blood flow, rate of filtration with backfiltration and access needle size used or catheter type (which effects venous pressure of returning blood at outlet 42).

The blood side pressure drop is dependent on blood flow and the size of the venous needle used to return the blood to the patient's body (using a smaller venous needle will result in a higher pressure leaving chamber 2), but can be approximated, for chamber 4, as a pressure drop, between chambers 34 and 38, of 40% of the pressure entering the dialyzer fibers (header pressure, chamber 34). For example, if the incoming pressure is 402 mmHg and the outgoing is 240 mmHg this is a difference of 162 mmHg, or 40% (=162/402), and approximately a 45% pressure drop of the pressure in chamber 38 to the exit chamber 30 (pressure drop across Chamber 2). The pressure drop in Chamber 2 will vary dependent on blood flow and rate of backfiltration, a higher blood flow resulting in relatively lower pressure drop as In the operation of a dialyzer according to the invention, a blood flow pressure drop between chambers 34 and 38 was measured to be 72% at blood flows of 400 ml/min and 90% at blood flows of 200 ml/min.

The double dialyzer according to the invention has two separate bundles of fibers for filtration, with fiber bundle headers at the ends of the chambers. Manifolds 24, 26 and 28 may be constituted by potting compound bodies. U.S. Pat. No. 4,227,295 (Bodnar) and U.S. Pat. No. 5,700,372 (Takesawa), the disclosures of which are incorporated herein by reference, describe common methods to manufacture dialyzers using the potting compound to form manifolds. This method can be used in the fabrication of a dialyzer according to the present invention. The fibers enter and exit through these bodies so that the blood encounters some resistance upon entering the fibers and the resistance at the entry to each fiber bundle aids filtration.

The potting compound is used to separate the internal pathways presented by the fibers from the dialysate compartments. This is done by inserting the fiber bundles into the dialyzer casing. Thus, a lower end header cap will be provided. The potting compound bodies are formed in place before the top and bottom header caps are put in place. To form the potting compound bodies, a special cap is clamped on each end of the casing and potting compound (polyurethane material) is injected into the special caps and around the fibers. The chambers are usually spun in order to distribute the potting compound so as to reliably form seals between the dialysate side and blood side of each chamber. Since blood flowing out of the fibers of bundle 14 will flow through chamber 38 and into the fibers of bundle 12, potting compound seals will be formed around the fiber ends that will extend into chamber 38, as well as around the fiber ends that will extend into compartments 30 and 34, after which the fiber bundle ends projecting from the potting compound bodies may be sliced off. The header caps may then be assembled to the ends of the casing.

Two separate dialysate compartments are provided in order to be able to provide the flow constriction 22 therebetween to control the rates of filtration and backfiltration. In fact, the flow constriction between dialysate compartments, near the bottom of wall 20, is a key component of the double dialyzer according to the invention. If the flow constriction yields too low of a pressure drop, the machine will alarm for low TMP because the average dialysate pressure will be too low for the amount of filtration the system produces. If the pressure drop across the flow constriction is too high (too small of a passage cross section), the dialyzer could clot as the TMP of fiber bundle 14 in chamber 4 increases (because of very low dialysate pressures), causing additional ultrafiltration of plasma water and hemoconcentrating the blood in chamber 4.

By having two separate bundles of fibers for blood and dialysate, it becomes possible to maintain a counter-current flow between dialysate and blood through the entire double dialyzer system, maximizing diffusive removal of blood toxins.

The parameters presented herein have been found to produce good results. However, variations are possible within the framework of the invention. For example, the membrane fibers can have a smaller ID, and/or thinner walls, and/or smaller or larger fiber membrane surface areas (e.g., 0.9 to 1.8 m$^2$ for each bundle). It is possible to have a difference in area between the two fiber bundles. This could be, for example 1.3 m$^2$ for bundle 12 and 1.5 m$^2$ for bundle 14, although this may make manufacturing more difficult. Unequal surface areas may also have to be balanced by possibly changing the filtration capability of the fiber bundles. If a fiber bundle having a smaller surface area were provided in one chamber, this may need to be compensated with a higher filtration capability in order to provide the correct filtration and backfiltration. If the inner diameter of each fiber were made smaller, the result would be an increase in pressure drop and an increase in filtration. There are numerous possible configurations.

Other variations, such as lower Kuf of the fiber bundles with higher pressure drops of the inter-dialysate chamber constriction are also possible, as well as higher Kuf and lower pressure drops. However, such variations should be within a small range to reach the optimal 25%-35% of blood flow filtration. For example, a Kuf of 10 with a blood flow of 500 ml/min would require a TMP of 750 mmHg; however the limit for TMPs for the membranes is usually around 500 mmHg or they could break. Similarly, a Kuf of 30 requires a maximum TMP of 250 mmHg; however at a 500 ml/min blood flow rate, the minimum TMP achievable is about 300 mmHg. The TMP referred to is the actual measured TMP at the inlet and outlet of both blood side and dialysate side, not the machine calculated TMP.

The size of the pores and the number of pores will determine the Kuf of the membrane.

The constricted passage 22 in wall 20 is important because if there were no constriction, the pressure at dialysate outlet 46 would be substantially equal to the pressure at dialysate inlet 44, so that there would be less filtration with backfiltration. Therefore, clearance of middle weight toxins would be reduced and there would also be problems with the dialysis machine because the dialysate pressure at outlet 46 would be higher than if the constricted passage was present. This higher pressure at outlet 46 will result in a reverse TMP alarm.

Also, a double fiber bundle with similar parameters but smaller total membrane surface areas (0.3 to 0.9 m² for each bundle) can be used to provide a hemodiafiltration treatment at lower blood flows (200 ml/min) and lower dialysate flows (100-400 ml/min). The constricted passage, i.e. opening 22, between dialysate compartments will still be required in order to drop the average of the dialysate side pressures to allow the double fiber bundle dialyzer system to run on standard equipment and will have diameter in a range as described earlier herein.

Distribution rings, or dialysate diverters, commonly used in this art, may also be provided near the inlet and outlet of dialysate ports 44 and 46, below manifolds 24 and 26, and at the bottom of the chambers, above manifold 28, to aid in distribution of the dialysate around the fibers. Examples of such diverters are disclosed in U.S. Pat. Nos. 4,396,510; 5,084,244; and 6,623,638, the disclosures of which are incorporated herein by reference.

The casing shown in FIG. 2 is provided with diverters 52, 53, 54 and 55, which may be integral parts of the casing. Dialysate entering via inlet 44 flows around diverter 52 and upwardly over the upper edge of diverter 52 before entering the dialysate compartment in chamber 2. Similarly, dialysate exiting from opening, or passage, 22 will be diverted under the lower edge of diverter 55 before entering the dialysate compartment in chamber 4. Diverters 53 and 54 are also used to aid in dialysate flow distribution by forcing the fluid to flow from the center of the dialyzer over the diverter to the periphery where dialysate will flow through restricted passage via diverter 53 and to port 46 via diverter 54. Since channeling commonly occurs along the walls of the chambers, the diverters force the dialysate away from the walls to the center where the fibers are located.

Figure 5:
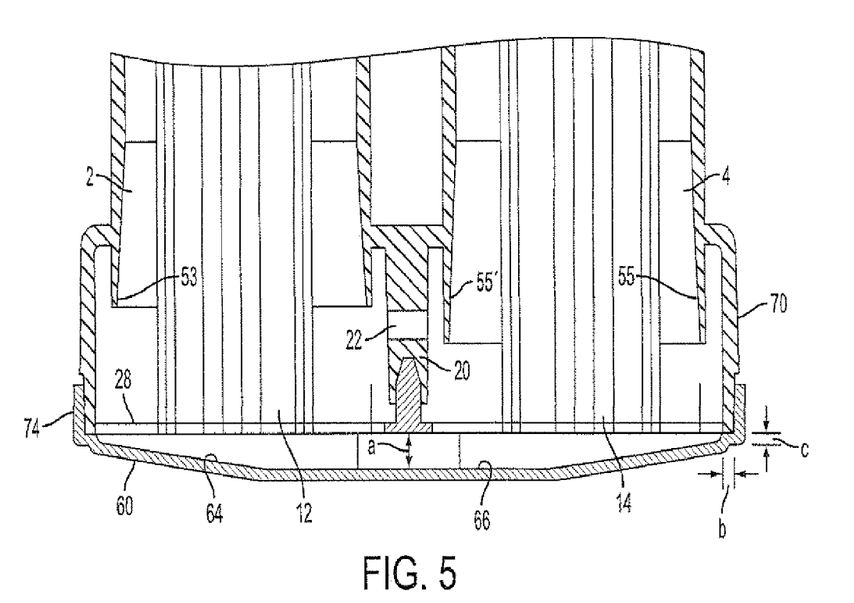
FIG. 5 is a cross-sectional view in the same plane as FIG. 4 showing the end cap of FIG. 4 connected to the dialyzer casing shown in FIG. 2.

FIG. 5 shows circular diverters 53 and 55 on each side of the passage 22. The dialysate exits from passage 22 at a higher velocity than the dialysate flowing through the chambers because of the small diameter of passage 22. To prevent damage to the fibers in bundle 14 due to the high velocity with which dialysate exits passage 22, the dialysate should contact the diverter, i.e., at diverter portion 55', then be distributed around the fiber bundle 14.

In addition, the lower end of diverter 53 is at a height at or above the upper longitudinal edge of passage 22, i.e., does not intersect the longitudinal projection of the cross section of passage 22, to allow a passage extending at an angle of 90° to the longitudinal axis of each chamber to be formed, e.g., drilled, by a suitable tool introduced from the side of chamber 2. If the lower edge of diverter 53 were to extend lower, then passage 22 could only be formed at an angle to the chambers in order to allow a pin or drill bit to be introduced during the manufacturing process. The dialysate passing through passage 22 will then hit diverter 55 and protect the fibers 14 from damage. Another possible configuration is to eliminate diverter 53 and have only have diverter 55.

Figure 4:
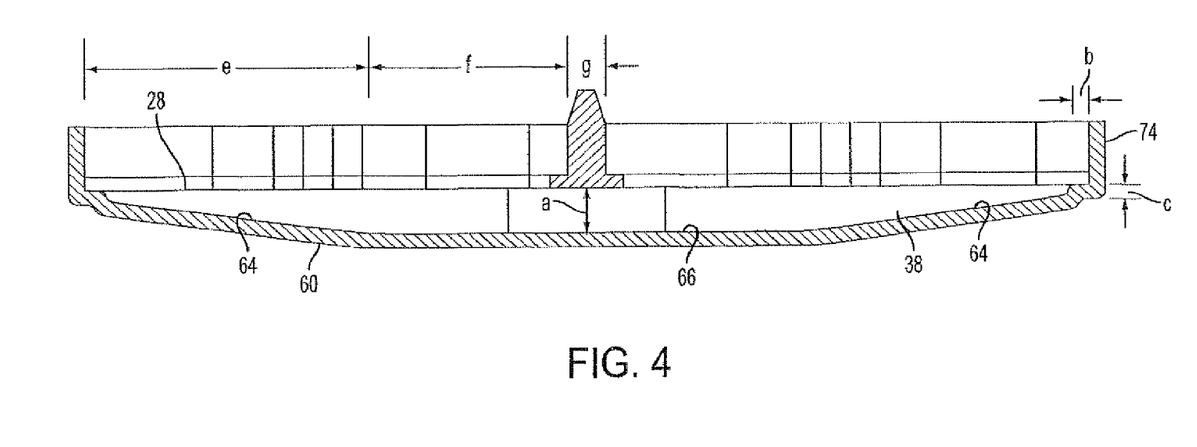
FIG. 4 is an elevational, cross-sectional view of a dialyzer bottom header cap, or end cap, according to the invention.
Figure 6:
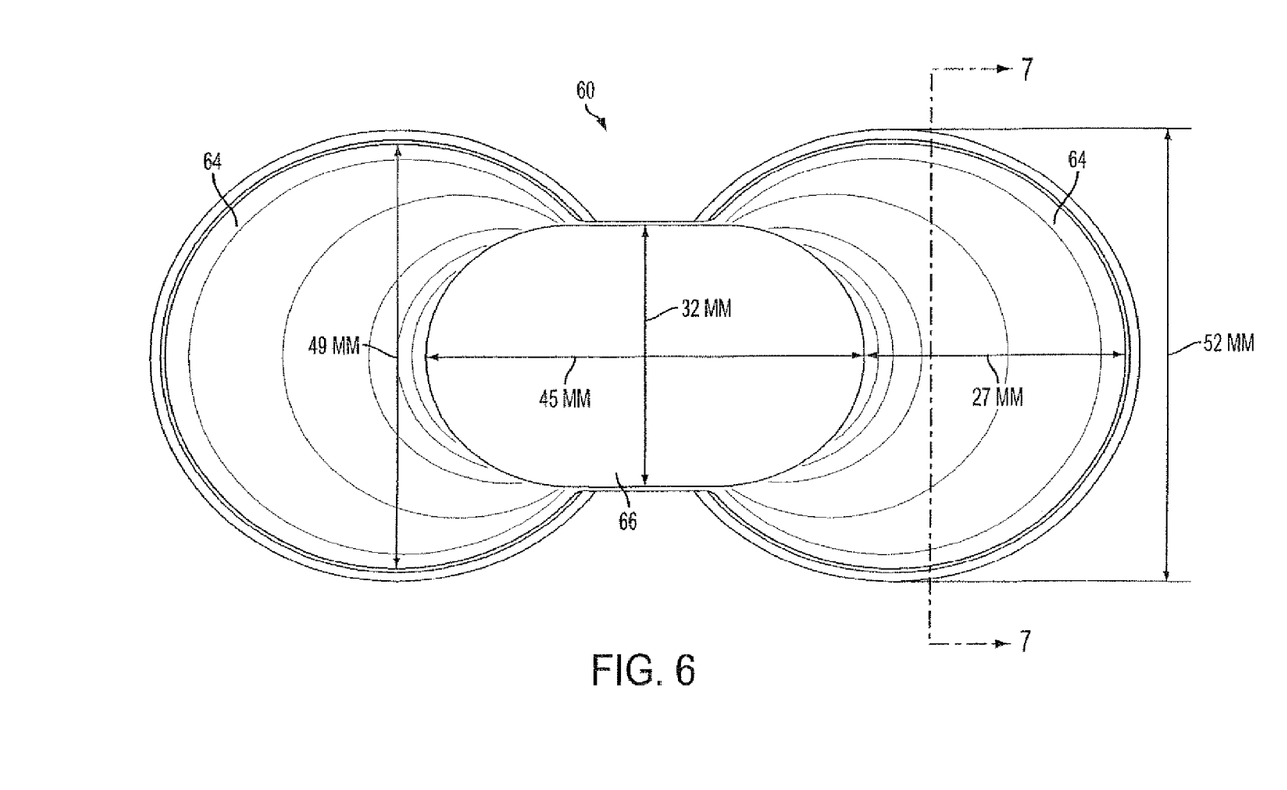
FIG. 6 is a plan view, in a plane perpendicular to that of FIGS. 4 and 5, showing the bottom surface of an end cap according to the invention.
Figure 7:
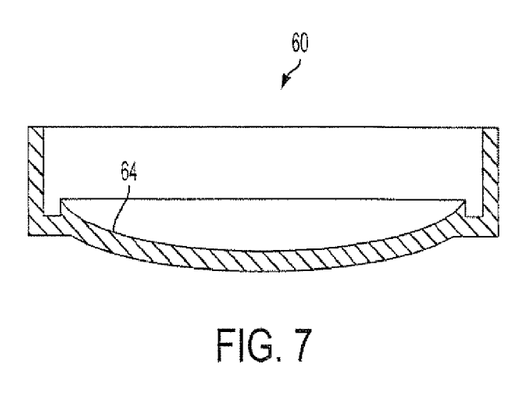
FIG. 7 is a cross-sectional view along plane 7-7 of FIG. 6.

FIGS. 4-6 illustrate a preferred embodiment of a novel end cap 60 according to the present invention.

According to the present invention, end cap 60 is constructed in such a manner as to present an intermediate blood flow path that produces a blood flow that is as uniform as possible in each plane perpendicular to the blood flow direction. For this purpose, the blood flow path is essentially free of surfaces having a small radius curvature and is composed essentially of flat radially extending surfaces and circular side surfaces.

The primary objective of the flow path in end cap 60 is to provide an atraumatic blood flow path that minimizes the potential for cellular lysis or thrombus formation. It is also constructed to keep the pressure losses through the end cap low, which helps to provide a low overall pressure drop through the hemodiafiltration device.

According to the invention, the potential for blood trauma in the flow header is minimized by eliminating regions of high blood shear stress where cellular lysis could occur. Also, the blood flow path is constructed to remove regions where the blood is exposed to very low, sustained blood shear stress near the end cap walls where blood thrombus (i.e. blood clotting) could form and grow. These sustained low shear stress regions can be visualized as flow re-circulation zones.

To achieve the improvements according to the invention, the blood flow path is shaped to gently change the direction of the blood flow, thus minimizing flow accelerations and decelerations within the end cap. To accomplish this goal, a flattened end cap structure with a wide interconnecting flow path area between the two fiber bundles is provided, as shown in the drawings. With this structure, the blood flow can transition smoothly and uniformly between the two fiber bundles. The more uniformly distributed end cap flow not only reduces the potential for re-circulation regions in the downstream portions of the blood flow path, but also reduces the frictional pressure losses through the end cap.

As shown in FIG. 4, the blood flow path between chambers 2 and 4 is defined essentially by chamber 38 formed in end cap 60. Chamber 38 is bounded, in the axial direction of chambers 2 and 4, by manifold 28. End cap 60 has a blood inlet and a blood outlet, side walls and a base that extends transversely to the side walls and surfaces, or walls, 64 and 66 formed by end cap 60. Surface 66 is at the center of end cap 60 and lies in a plane that is perpendicular to the longitudinal axis of chambers 2 and 4. Surfaces 64 extend outwardly from surface 66 to the periphery of end cap 60 and are inclined at a shallow angle to the plane of surface 66. An exemplary value of this shallow angle can be calculated from exemplary dimensions presented below. Surfaces 64 are inclined in a direction that causes the height dimension of chamber 38, in the direction of longitudinal axis of chambers 2 and 4, to decrease from the junction with surface 66 to the lateral edges of end cap 60.

As shown in FIG. 6, which is in a plane perpendicular to that of FIGS. 4 and 5, compartment 38 (FIG. 4) is bounded laterally by side walls having the form of portions of circles and constituted by wall portions 70 (FIG. 5) that extend from the outer casings that delimit chambers 2 and 4. Flat surface 66 has the general form of an oval with semicircular ends and linear longitudinal portions between the ends.

As shown particularly in FIGS. 4 and 5, end cap 60 further includes side walls 74 that surround wall portions 70 and conform in shape to wall portions 70. Side walls 74 are bonded to wall portions 70 in any suitable manner such as with a potting compound and without the use of O-rings. FIGS. 4 and 5, which illustrate certain dimensions for end cap 60, exemplary values for the dimensions indicated are the following: a=6 mm; b=2 mm; c=3.0 mm; e=22.5 mm; f=26.5 mm and g=4 mm. However, the invention encompasses other dimensions that have a comparable influence on blood flow.

Slanted surface 64 of the header cap under chamber 2 helps to push blood and air into fiber bundle 12, the air then flowing upwardly with the blood in the fiber bundle and then flowing out if the dialyzer through cap 30. This helps in priming the dialyzer (filling the dialyzer with saline to get the air out) prior to patient treatment and helps eliminate any air in the system that may not have been removed during priming, but is pushed through by the more viscous blood.

When the dialyzer is being used, it will be oriented so that end cap 60 will be at the bottom, i.e., below chambers 2 and 4. As a result, blood will flow downwardly in fiber bundle 14, across end cap 60 and then upwardly through fiber bundle 12. This helps to remove air bubbles from the dialyzer fibers, which, when blood exits the fiber bundle 12, are caught in the bubble chambers of the blood lines (not shown), which are a standard part of blood lines, preventing any air bubbles from reaching the patient.

Double fiber bundle dialyzers according to the present invention work by having large volume ultrafiltration in fiber bundle 14 of FIG. 1, to receive blood, with similar volume backfiltration across the membranes in fiber bundle 12 of FIG. 1. The desirable rate of ultrafiltration and backfiltration are dependent on the blood flow with the upper limit of ultrafiltration being equal to approximately 35% of the blood flow, depending on the hematocrit (ratio of volume of blood cells to total volume of blood).

If, for example, the blood flow into the dialyzer is 400 ml/min, the amount of ultrafiltration (and backfiltration) equals approximately 140 ml/min (35%×400 ml/min). If the hematocrit enters at 32% (common for dialysis patients), the peak hematocrit will reach 49%, before the backfiltration returns the hematocrit to near 32%.

During dialysis treatment, the hematocrit naturally increases as excess fluid is removed from the body. It is not uncommon for a patient's hematocrit to increase from 32% at the start of dialysis to 38% at the end of a dialysis treatment. If one were to remove 140 ml/min when the entering hematocrit is 38%, then the peak hematocrit will be 58%, which is too high and may result in clotting of the dialyzer. However, as the hematocrit increases, so does the oncotic pressure of the blood (forces due to blood proteins that hold onto the plasma water). This reduces the amount of fluid that is ultrafiltered across the membrane. At an entering hematocrit of 38%, the same membrane may result in lower ultrafiltration, perhaps only 25% of the blood flow due to the increase in oncotic pressure.

The amount of fluid that is ultrafiltered in the first fiber bundle of the double fiber bundle dialyzer will depend on the blood flow rate, dialysate flow rate and the hematocrit of the blood. The type of membrane used will also affect the volume of ultrafiltration. The restricted orifice 22 is required in order to produce a suitable pressure difference between the dialysate compartments of the bundles. Too large of an orifice and the bundles act as one long compartment, too small of an orifice and the pressure becomes too high and causes machine problems and excess ultrafiltration/backfiltration. There are membranes that differ from one another in ultrafiltration capability dependent on their structure. High flux membranes have larger pore sizes, up to 50 k Daltons, with some new membranes even higher. Low flux membranes have smaller pore sizes, sometimes only up to 15 k Daltons. The removal of molecules is therefore size dependent and the cutoff, at 15 k Daltons, is the largest pore size. The ability to remove the middle sized molecules is evident in membrane manufacturer literature that shows the sieving coefficients of middle sized molecules, e.g., Cytochrome C (12,233 Daltons). The number of the larger sized pores will also affect the ultrafiltration by membranes. Other factors that affect ultrafiltration include the inner diameter of each hollow fiber strand, the wall thickness of each hollow fiber strand and the geometry of the pores.

The amount of ultrafiltration for a given membrane depends on the pressure of the blood on the blood side of the membrane (hydrostatic pressure) pushing fluid across the membrane, the pressure on the dialysate side of the membrane preventing fluid from fluxing across the membrane, and the pressure of the blood holding onto the fluid (oncotic pressure). The sum of these pressures is equal to the transmembrane pressure (TMP). Membranes can be evaluated by coefficient of ultrafiltration (Kuf), which is the amount of ultrafiltration in ml/hour/mmHg TMP.

The goal of the double fiber bundle dialyzer is to remove middle sized molecules efficiently (10 k up to approximately 50 k Daltons) by means of convective removal (flux of the fluid across the membrane). In order to do this, a high flux membrane must be used in the first fiber bundle. However, high flux membranes have high Kuf values. Given the pressures generated by the blood pumping into the dialyzer, there is a concern that the ultrafiltration rate will be too high (greater than 35% of blood flow), and the blood will hemoconcentrate and clot. If the membrane flux is too low, the rate of middle molecule removal will be poor (due to poor sieving coefficient and low volume) and this will adversely affect the advantage of using the double fiber bundle dialyzer over standard dialysis.

The second fiber bundle is where backfiltration occurs. This is filtration of fresh dialysate fluid that enters the dialyzer and fluxes the membranes of bundle 12 to replace the fluid volume that was removed (ultrafiltered) from the first fiber bundle 14. Ideally, since dialysate fluid is pumped across the membrane into the blood, this membrane should prevent microorganisms from crossing the membrane. The tighter, or smaller, the pore size, the lower the flux and the sieving coefficient and the safer the backfiltered fluid, i.e., the lower possibility of bacteria or other toxins crossing the membrane due to smaller mean, median and mode of the pore size.

However, if the pore size is too small, not enough fluid will backfilter and the dialysis machine will alarm that there is a fluid balance error in the system.

The dialysis machine makes sure that the volume of dialysate leaving the dialyzer is equal to the volume of dialysate entering the dialyzer. There are a few different ways this can be achieved.

The Phoenix machine, by Gambro Healthcare, uses two flow sensors that measure the incoming and, separately, the outgoing dialysate volumes. It then compares the two volumes and adjusts the rate of dialysate fluid leaving the dialyzer and returning to the machine to keep the two volumes even.

The Fresenius machines use two balancing chambers where the fluid leaving the dialyzer and returning to the machine are always in balance. As the dialysis machine insures the balance of the fluid leaving and entering the dialysis circuit, the pressure of the dialysate returning to the machine (leaving the dialyzer) will vary.

It is possible to have a negative pressure on the dialysate line leaving the dialyzer, returning to the dialysis machine, which increases the volume of ultrafiltration in the first fiber bundle. Similarly, if the volume of plasma water ultrafiltered across bundle 14 is too high, the dialysate line pressure will increase, reducing the TMP and, consequently, the amount of ultrafiltration across bundle 14.

In the double fiber bundle dialyzer, one way to ensure similar volumes of ultrafiltration and backfiltration is to have membranes with similar Kuf (ultrafiltration capabilities). In-vitro studies have demonstrated that the TMP generated in the first fiber bundle 14 is on the order of 275 mmHg at 400 ml/min blood flow. Given a mid flux membrane with a Kuf=20, one would expect an ultrafiltration rate of (20×275)/60=92 ml/min which is close to a 25% ultrafiltration rate at 400 ml/min flow. However, it has also been shown that membranes with a Kuf=20 do not have good middle molecule removal, with a low sieving coefficient for molecules larger than 5000 daltons. A Membrana® membrane bundle tested with Kuf=20 had poor removal of myoglobin, a middle molecule of approximately 17 k Daltons. Though the ultrafiltration and backfiltration were within the desired range (up to 35%), the removal of the middle weight toxins was less than desired.

Alternatively, the use of two high flux membranes (Kuf=65) resulted in ultrafiltration rates greater than 40% of the blood flow. This raises the risk of clotting during the treatment.

Using either two low flux membrane bundles or two high flux membrane bundles in the double fiber bundle dialyzer resulted in increasing rates of ultrafiltration as dialysate flows increased. Increasing dialysate flows also resulted in lower dialysate out pressures at outlet 46 in FIG. 1. As the dialysate entered at a higher flow rate and pressure, more fluid was fluxed across the membrane of bundle 12, requiring more fluid to be removed across bundle 14. Therefore, if a mid flux membrane is used for bundle 12, a higher Kuf membrane can be used for bundle 14. This combination also permits improved removal of middle molecules across the fiber bundle 14 and a tighter membrane for the backfiltration in fiber bundle 12. The dialysis machine will ensure the amount of dialysate leaving the dialyzer is equal to the volume entering the dialyzer (plus some additional volume for fluid removal from the patient due to weight gain).

Restrictor 22 is needed in all of these configurations because without the restricted orifice, there is not enough of a pressure drop between the dialysate side of the two compartments to cause a shift in ultrafiltration and backfiltration. The machines will also alarm with a backfiltration alarm or low TMP alarm as the dialysate out pressure (out of the dialyzer) is higher (no pressure drop) and the TMP becomes higher on the dialysate side than on the blood side. It might be noted that blood side pressures are commonly measured by using only the venous pressure (blood out).

In-vitro studies were performed using high flux membranes in the first fiber bundle (Kuf=65) and mid flux membranes (Kuf=20) in the second fiber bundle. At blood flow rates of 300, 400 and 500 ml/min with dialysate flows of 500 ml/min, ultrafiltration rates were 35%, 32% and 29%, respectively. As expected, the rate of ultrafiltration increased when dialysate flows were increased (40%, 36%, and 33% for blood flows of 300, 400 and 500 ml/min respectively).

The removal of middle weight molecules can be optimized according to the invention by the provision of a double fiber bundle dialyzer with restrictor 22 having a diameter of 2.0 mm or less and flux membranes with different characteristics such that fiber bundle 14 has a Kuf greater than or equal to 30 ml/h/mmHg TMP per $m^2$ and fiber bundle 12 has a Kuf equal to or less than 20 ml/h/mmHg TMP per $m^2$. ($m^2$=square meter surface area.

The present invention is also embodied in a dialysis method that includes altering the rate of filtration in the double dialyzer by changing the dialysate flow rate. Increasing the dialysate flow will increase the filtration rate, and decreasing the dialysate flow will reduce the filtration rate. At a higher dialysate flow, more fluid is fluxed across bundle 12 and the machine compensates by decreasing the dialysate side pressure of chamber 4, allowing more fluid to flux from blood to dialysate of in bundle 14.

According to one example of this method, a dialysis procedure may start with a dialysis treatment at the low end of normal dialysate flow rate (e.g., 500 ml/min) and increase the dialysate flow rate in subsequent treatments while keeping machine TMP in an acceptable range (<300 mmHg TMP). Also, removal of middle molecule (e.g., B2 microglobulin) can be used as a marker of filtration rate.

Dialyzers according to the invention may be provided with high molecular weight cutoff membranes (65 k Daltons and higher, which membranes also have very high Kuf) in the fiber bundle 14, with a mid to low flux membrane in fiber bundle 12 to control rate of ultrafiltration. This therapy will help maximize the removal of pro-inflammatory cytokines, treat myeloma kidney, sepsis and rhabdomyolysis. This configuration can also be used to remove protein bound solutes, if clinically required. This configuration can also be used to remove protein bound solutes, if clinically required.

This present invention may also be used with the specialized dialysis machines capable of delivering HDF treatments. The use of pre-dilution HDF (fluid infused before entering the dialyzer) using the present invention as the dialyzer will deliver a rate of filtration equal to or greater than the amount of filtration of which a standard HDF dialyzer in the same pre-dilution modality is capable.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A dialyzer comprising:

first and second dialyzation chambers, and an end cap delimiting an intermediate chamber interposed between said first and second dialyzation chambers, wherein, each of said dialyzation chambers has opposed first and second ends;

each of said dialyzation chambers contains a filter member that separates said chamber into a blood compartment and a dialysate compartment, each of said compartments extending between said first and second ends;

said filter member in said first chamber is made of a filter material for filtering out plasma water from blood;

said filter member in said second chamber is made of a filter material for passing dialysate from said dialysate compartment to said blood compartment;

said first chamber has, at said first end thereof, a blood inlet communicating with said blood compartment and a dialysate outlet communicating with said dialysate compartment;

said second chamber has, at said first end thereof, a blood outlet communicating with said blood compartment and a dialysate inlet communicating with said dialysate compartment;

said intermediate chamber extends between said second end of said first dialyzation chamber and said second end of said second dialyzation chamber and communicates only with said blood compartments;

said blood and dialysate inlets and outlets are located to produce dialysate flows in counter-current to blood flows in both of said chambers; and said first and second chambers are constructed to provide a constricted passage providing a dialysate flow path, wherein said end cap is secured at the second ends of said first and second dialyzation chambers to conduct blood through said intermediate chamber between said dialyzation chambers, wherein said end cap comprises:

blood inlet and outlet openings aligned with the second ends of the first and second dialyzation chambers; and side walls surrounding said blood inlet and outlet openings and having circular arcuate portions; and wherein said end cap (60) further comprises a base extending transversely to, and delimited by, said side walls, said base presenting first and second surfaces each aligned with a respective one of said blood inlet and outlet openings and a third surface extending between said first and second surfaces, said first and second surfaces each being inclined at an obtuse angle to said third surface; and said end cap (60) presents a wide interconnecting flow path between the dialyzation chambers and the third surface of the base of the end cap is a flat surface that has the general form of an oval with semicircular ends.

2. The dialyzer of claim 1, wherein said side walls of said end cap further include substantially straight portions extending between, and joined to, said circular arcuate portions.

3. An end cap constructed to be connected to a dialyzer composed of first and second dialyzation chambers each dialyzation chamber having opposed first and second ends and containing a filter member that separates the chamber into a blood compartment and a dialysate compartment, said end cap being constructed to be secured at the second ends of the first and second dialyzation chambers and presenting an intermediate blood flow chamber to conduct blood between the dialyzation chambers, wherein said end cap comprises:

blood inlet and outlet openings located to be aligned with the second ends of the first and second dialyzation chambers when said end cap is secured at the second ends of the first and second dialyzation chambers;

side walls surrounding said blood inlet and outlet openings and having circular arcuate portions; and a base extending transversely to, and delimited by, said side walls, said base presenting first and second surfaces each aligned with a respective one of said blood inlet and outlet openings and a third surface extending between said first and second surfaces, said first and second surfaces each being inclined at an obtuse angle to said third surface, wherein each of said first, second and third surfaces (64, 66) of said base is substantially flat and said end cap presents a wide interconnecting flow path between the dialyzation chambers and the third surface of the base of the end cap is a flat surface that has the general form of an oval with semicircular ends.

4. The end cap of claim 3, wherein said side walls of said end cap further include substantially straight portions extending between, and joined to, said circular arcuate portions.

* * * * *